June 20, 1933. C. C. CHAMBERLIN Plant Pat. 68
SNAP DRAGON
Filed April 1, 1932
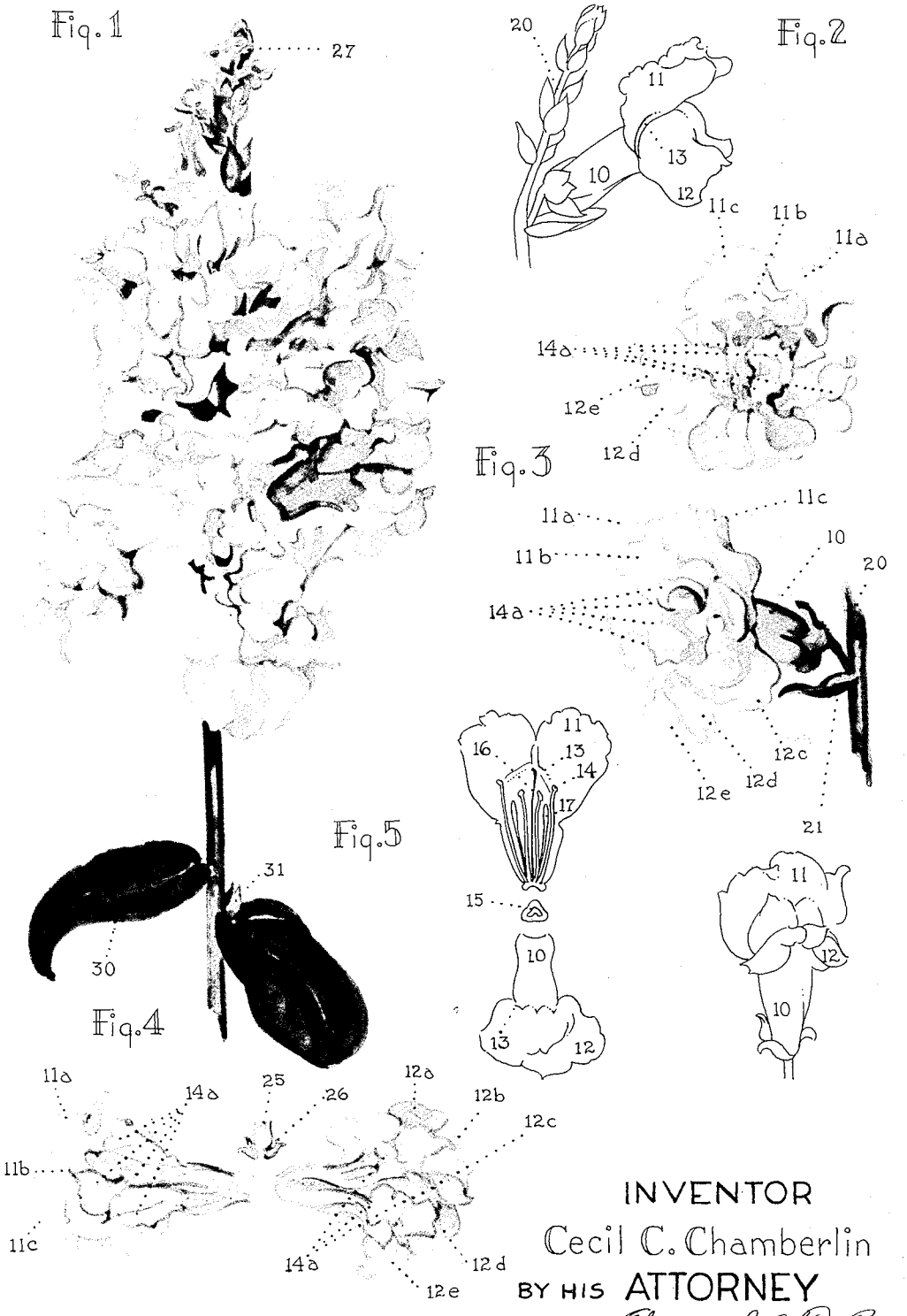
INVENTOR
Cecil C. Chamberlin
BY HIS ATTORNEY
Edmund J. De Pas Patented June 20, 1933 Plant Pat. 68

UNITED STATES PATENT OFFICE

CECIL C. CHAMBERLIN, OF CHAGRIN FALLS, OHIO

SNAP DRAGON

Application filed April 1, 1932. Serial No. 602,500.

This invention relates to plants and has special reference to a snap-dragon (antirrhinum) which I have produced and which is shown on the accompanying drawing wherein Fig. 1 is a perspective view, copied from a photograph; Fig. 2 is an enlarged side elevation of the usual single snap-dragon flower; Fig. 3 is a side view and a front view of one flower of my new plant; Fig. 4 illustrates the parts of one flower of my new plant; and Fig. 5 is a similar view illustrating the parts of one flower of the usual snap-dragon. The colors shown in the drawing constitute an accurate representation of the colors of my improved original plant and its descendants, this color being ordinarily characterized as bronze with yellow center; although the word "bronze" is to be taken rather in the sense in which it is employed by florists and flower growers than by that known in the metallic arts. Furthermore I do not limit myself to this color except in so far as is recited in my claims, inasmuch as the flowers seem to vary somewhat in this respect; also I do not limit myself to the exact shapes and appearances of the parts since the different flowers vary considerably not only in one plant but on one single flower-spike; yellow flowers are sometimes mixed with bronze.

My improved snap-dragon is characterized principally by a pronounced doubleness. Figs. 2 and 5 of my drawing illustrate the usual appearance and conformation of the flower of the snap-dragon. This flower ordinarily (and to the best of my knowledge and belief always heretofore) has comprised the following very characteristic parts: a "corolla-tube" 10 is formed at its upper end with oppositely disposed ears 11 and 12, whose bases are offset toward each other to define two lips which fit each other along the line 13 being ordinarily held shut by the elastic shape of the tube. The ears 11 and 12 constitute the showiest portion of the flower, being ordinarily more deeply colored than the tube and more conspicuous. Each of the ears is usually notched, the ear 11 having two lobes and the ear 12 usually having three lobes. Inside the closed tube are the stamens 14 and ovary 15 the latter having a style 16 rising into the tube. Usually the functional stamens are four in number but often there are also some vegetative processes 17 of stamen-like shape. These stamens and processes are attached to the base of the corolla-tube and are sometimes wholly enclosed though occasionally two functional stamens may protrude through the closed lips as shown in Figs. 2 and 5.

Usually these flowers grow singly in the angle between the stem 20 and bract 21. Higher on the same stem additional flower buds 22 usually occur which mature later, and below on the same stem one or two older flowers are often found but seldom more than six to ten at one time, since the older flowers adhere quite weakly and are readily shaken loose especially after the stalk is severed.

As against this, the prevailing and most essential characteristic of my improved snap-dragon resides in the fact that each flower shows a pronounced reduplication of the corolla lobes together with petal-like expansion of the stamens and vegetative processes all of which is popularly expressed by the word "doubling"; also a marked protrusion of these parts from the corolla tube; and secondarily that the flowers exhibit a far more tenacious hold upon the stalk than is observable in snap-dragons, so much indeed that the lower flowers have been known to stay in place for six to eight weeks in the case of stalks attached to the soil, while even when severed they usually resist separation at least a week to ten days. These two peculiarities, taken together, produce a display of greatly augmented magnificence, inasmuch as each individual flower is at least twice the diameter of previous snap-dragons, while the tenacity of their attachment increases the number of flowers carried by each stalk, at one time many fold producing massive spikes of brilliant color as much as a foot long and three inches in diameter when grown under favorable conditions.

The stalks themselves are extremely strong and sturdy, often standing when full grown something like four feet in height.

In addition to the modification of the sexorgans to petal-like form, the original corolla exhibits a greater complexity. In the particular flower illustrated in Figs. 3 and 4 the portion 11 instead of being divided into two lobes is formed into three, $11^a$, $11^b$ and $11^c$ each much larger than usual, crinkled and folded to find space, and having rougher and more irregular edges; also the portion 12 is formed into five lobes $12^{a-c}$, instead of three; the stamens and stamen-like processes are increased in number, and length, flattened and widened, and their anthers changed (sometimes wholly and sometimes only partially) to flaring, colored, petal-like elements. These are indicated at $14^a$ in Figs. 3 and 4, but there is no strict uniformity about them in different flowers, either number, shape or arrangement of color.

The ovary, which in the usual snap-dragon is a hollow organ containing numerous immature seeds is replaced by a curious kind of central bud 25, carried by a short pedicel 26 inside the corolla-tube; and this bud instead of seeds, shows a series of telescoped bracts and vegetative points which look as though they might under suitable conditions elongate into flower spikes.

At the upper end of each flower-spike is a tip 27 consisting of a series of unopened flower-buds with their accompanying bracts. With rich soil and forcing a substantial number of these can be matured at one time. I do not stress the color as being either new or important since feeding and selection cause the same to vary and the blossoms on one spike vary from bronze to yellow.

The leaves 30 are arranged irregularly alternately around the stem and in the axil of each leaf (or most of them) is usually found a bud 31 which when removed and placed first in water for a time and then in soil can easily be matured into a new plant. I do not assert that vegetive reproduction cannot be secured from other parts of the plant, but only assert that it can be secured by using these buds. The leaves and stems have thus far proven extremely resistant to rusts, blight and insect pests. I have produced many generations of propagation by asexual means. I do not yet know whether viable seed will be produced, or what if any proportion of the seed will retain the characteristics I have described, although I doubt if any reliable propagation will be possible except vegetatively.

The different flowers even on one and the same stalk exhibit a substantial degree of variation in respect of the number and arrangement of their parts. In some instances, for example, the anthers remain clearly distinguishable, in other instances they are wholly altered to flat, bronze-colored, petal-like shape and texture. In some cases they are wholly independent of the corolla-tube, in other cases they are united more or less completely thereto. In some blossoms the fundamental similarity to the usual snap-dragon is quite clear, in other blossoms the similarity is difficult to recognize. Accordingly I do not confine myself to any one criterion of identification.

Having thus described my invention what I claim is:

A snap-dragon substantially as herein shown and described characterized and predominantly distinguished by a substantial reduplication of the corolla-lobes and a protrusion from the corolla-tube of additional petal-like elements.

In testimony whereof I hereunto affix my signature.

CECIL C. CHAMBERLIN.